United States Patent [19]
Erskine

[11] Patent Number: 5,356,390
[45] Date of Patent: Oct. 18, 1994

[54] CATHETER INTRODUCER ASSEMBLY

[75] Inventor: Timothy J. Erskine, Way Sandy, Utah

[73] Assignee: Becton, Dickinson and Company, Franklin Lakes, N.J.

[21] Appl. No.: 130,067

[22] Filed: Sep. 30, 1993

[51] Int. Cl.⁵ .................................... A61M 25/01
[52] U.S. Cl. ........................ 604/164; 604/169; 604/249; 604/256
[58] Field of Search ........... 604/164, 171, 249, 256, 604/167, 247, 254, 169

[56] References Cited

U.S. PATENT DOCUMENTS

| | | | |
|---|---|---|---|
| 3,570,485 | 3/1971 | Kelly | 128/214.4 |
| 3,592,192 | 7/1971 | Harautuneian | 128/214.4 |
| 3,595,230 | 7/1991 | Suyeeka | 128/214.4 |
| 3,682,173 | 8/1972 | Center | 128/214.4 |
| 3,757,771 | 9/1973 | Ruegg et al. | 128/2.1 |
| 3,788,318 | 1/1974 | Kim | 604/164 |
| 3,985,140 | 10/1976 | Harris | 604/247 |
| 4,068,659 | 1/1978 | Moorehead | 128/214.4 |
| 4,160,450 | 7/1979 | Doherty | 128/214.4 |
| 4,205,675 | 6/1980 | Vaillancourt | 128/214.4 |
| 4,233,982 | 11/1980 | Bauer et al. | 604/256 |
| 4,676,783 | 6/1987 | Jagger et al. | 604/171 |
| 4,781,692 | 11/1988 | Jagger et al. | 604/164 |
| 4,808,158 | 2/1989 | Krevrier | 604/256 |
| 4,846,805 | 7/1989 | Sitar | 604/165 |
| 4,927,415 | 5/1990 | Brodsky | 604/164 |
| 4,969,876 | 11/1990 | Patterson | 604/171 |
| 4,976,697 | 12/1990 | Walder et al. | 604/164 |
| 5,064,415 | 11/1991 | Walder et al. | 604/164 |
| 5,250,034 | 10/1993 | Appling et al. | 604/256 |

*Primary Examiner*—Paul J. Hirsch

[57] ABSTRACT

A catheter introducer assembly is disclosed. The assembly is made up of a winged catheter introducer having a catheter, an intermediate member attached to the catheter and a flexible tube attached to the intermediate member. Disposed axially within the catheter is a sharp needle. The needle is secured to a stylet which in turn is connected to a bead. The bead is slidable in the tube. Secured to the outside of the tube is a hard tubular section. A retractor is slidably mounted to the outside of the tube. The retractor confines the bead such that when the retractor slides along the outside of the tube, the bead slides along the inside of the tube. The retractor is provided with ribs shaped such that the retractor can be moved along the tube in one direction only. When the needle is retracted, its sharp tip is aligned with the hard tubular section. The needle is thus secured within the tubular section.

15 Claims, 4 Drawing Sheets

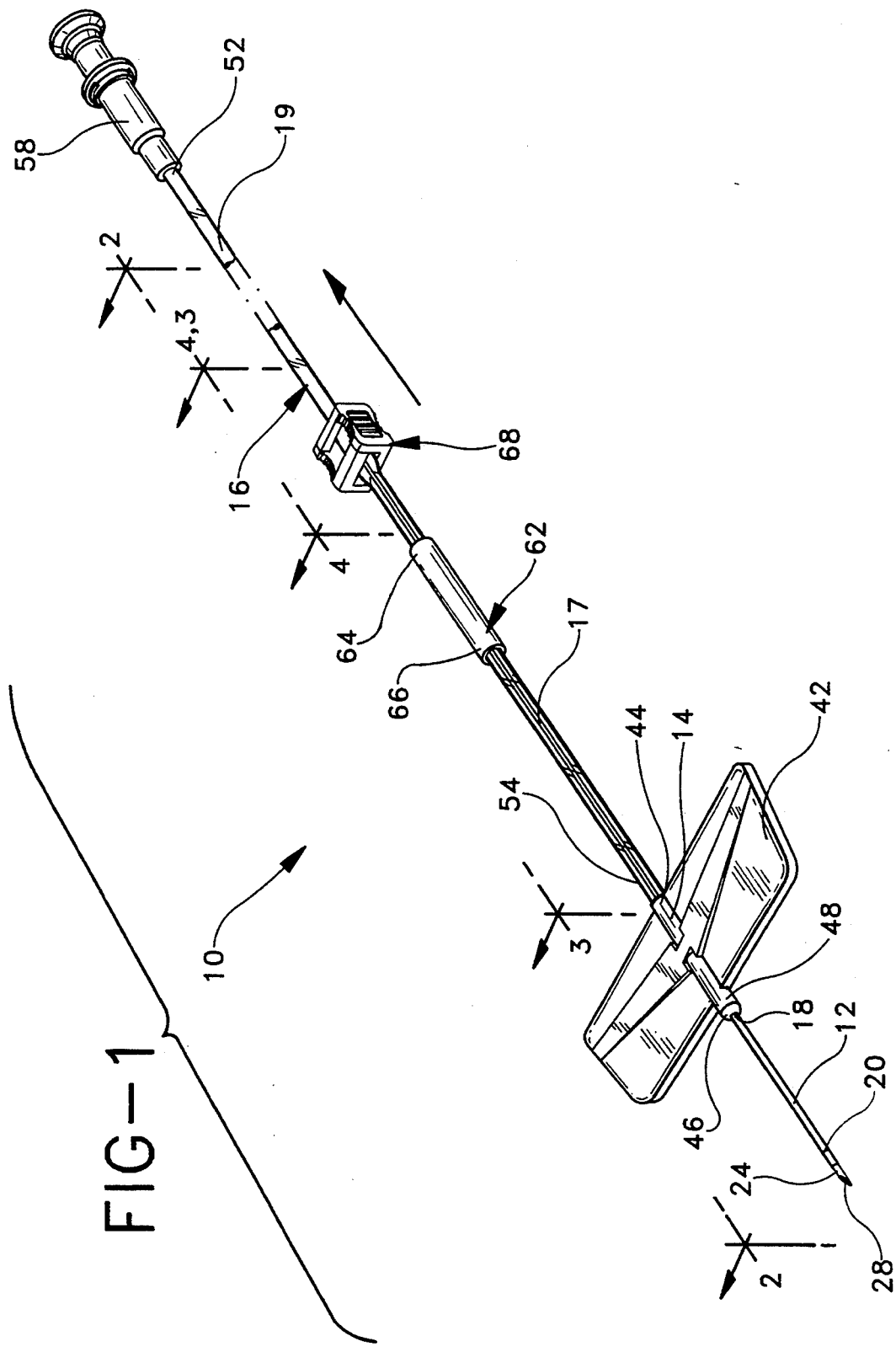

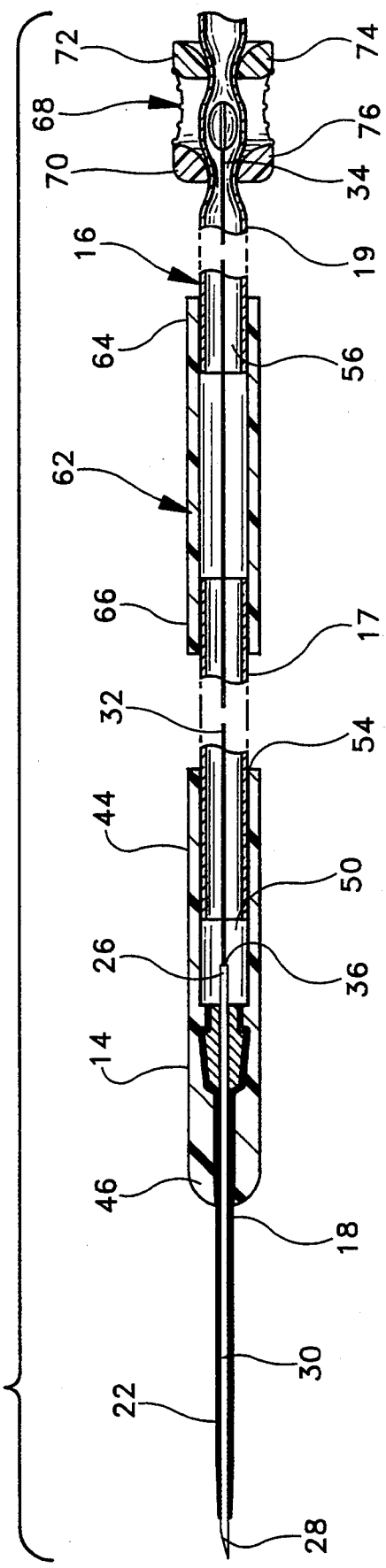
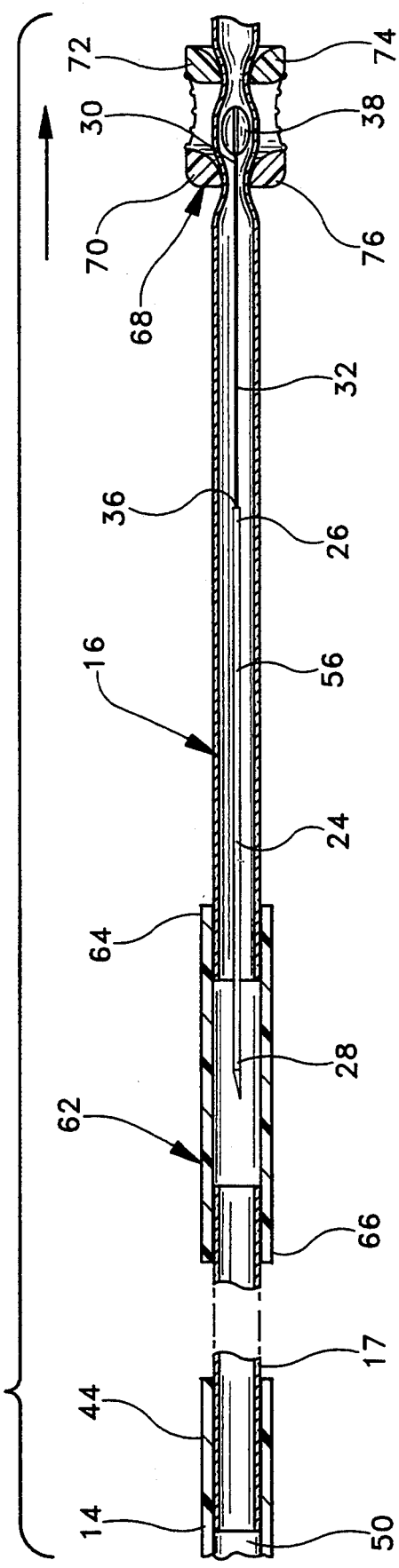

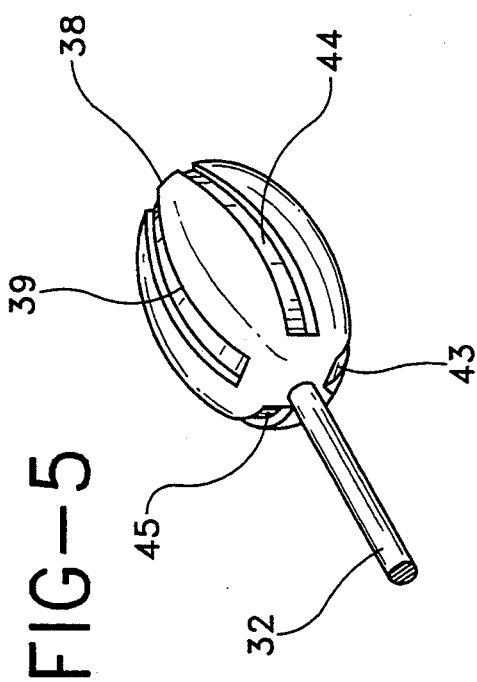
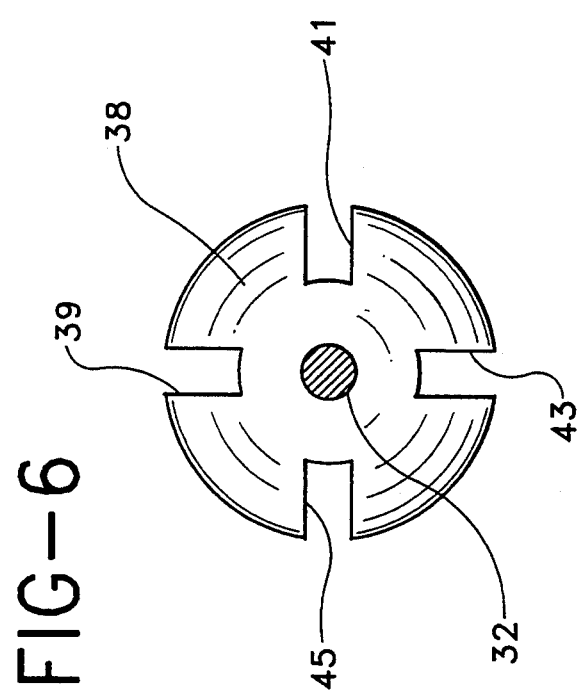
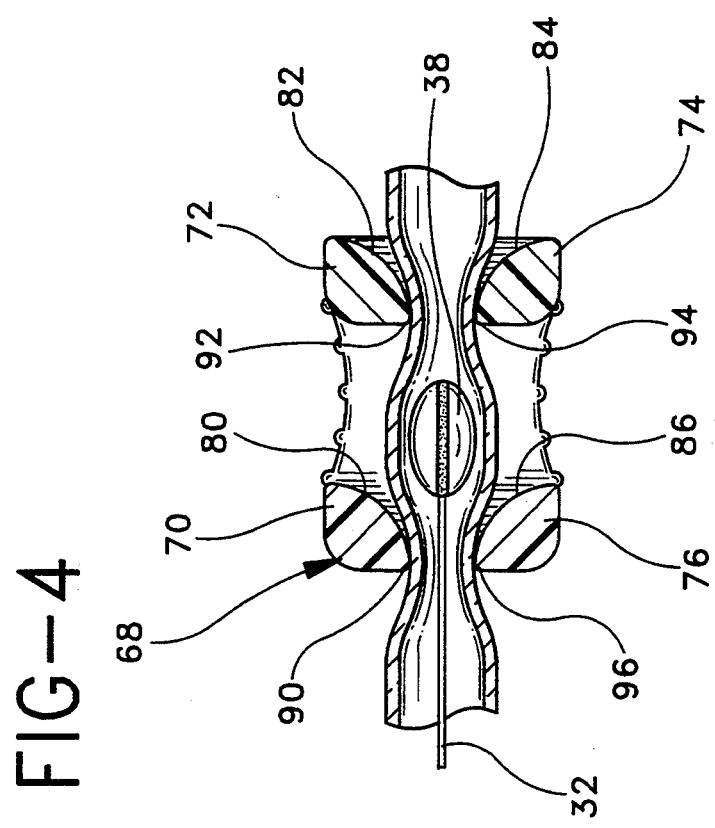

CATHETER INTRODUCER ASSEMBLY

BACKGROUND

This invention relates generally to the field of vascular access catheters. More specifically, it relates to a catheter introducer assembly having a special mechanism for retracting the introducer needle and shielding the introducer needle after introduction of the catheter into a blood vessel.

Vascular access catheters are commonly used in the medical and surgical arts for gaining access to the vascular system of a patient, for example, to infuse fluids into a patient's blood vessel. Such devices are introduced into the blood vessel by means of a sharp needle. The needle makes an initial opening in the vessel. Once the needle has successfully penetrated the vessel, a catheter is threaded over the needle and into the blood vessel. The needle is then withdrawn from the blood vessel with the catheter remaining in the vessel.

Since such a procedure necessarily involves contact between the needle and the patient's blood, there is a risk that the needle will infect third parties if the patient is infected with a blood borne disease such as AIDS or hepatitis. Since the incidence of AIDS and hepatitis has increased in recent years, there has become an increased awareness of the risks posed by catheter introducer needles. For this reason, several attempts have been made to design catheter introducers which shield catheter introducer needles.

This invention relates to a particular class of catheter introducer, namely introducers of the type sold by Becton Dickinson and Company of Franklin Lakes, N.J. under the trademarks Angioset ® and Intima TM. Such catheter introducers are described in U.S. Pat. Nos. 4,177,809 and 5,163,913 which are incorporated herein by reference. The Angioset ® and Intima TM devices comprise a catheter, a tube and a needle and stylet disposed in the catheter and tube. Once the catheter has been introduced into the blood vessel, the needle is withdrawn by pulling the stylet. When the needle is fully withdrawn, the needle and stylet can be disposed of. When such a procedure is employed, the needle and stylet may be contaminated with blood. There is therefore a need to provide a catheter introducer of the Angioset ® and Intima TM type which avoids the risk of blood contamination by the needle and stylet.

SUMMARY OF THE INVENTION

The invention is a catheter introducer assembly. The assembly is made up of a catheter having a proximal end, a distal end and a lumen extending there between. A flexible tube is in fluid communication with the lumen of the catheter. The tube has a proximal end and a distal end and a lumen extending there between. An introducer needle is axially disposable in the catheter lumen. Connected to the proximal end of the needle is an object which partially occludes the tube and is slidable in the tube. Squeezing the tube adjacent the object causes the object and hence the needle to move axially in the lumen of the tube.

The invention also contemplates a method of retracting a catheter introducer needle. The method comprises the steps of: connecting the catheter introducer needle to an object; enclosing the object within a flexible tube; squeezing the tube near the object; and, imparting a substantially axial force to the tube such that the force is transmitted to the object, thereby moving the object axially along the tube and retracting the introducer needle.

BRIEF DESCRIPTION OF THE DRAWINGS

FIG. 1 is a perspective view of the invention with the tip of the catheter introducer needle exposed;

FIG. 2 is a cross section of the invention through section 2—2 of FIG. 1 with the tip of the introducer needle exposed;

FIG. 3 is a cross section of the invention through section 3—3 of FIG. 1 showing the introducer needle retracted;

FIG. 4 is a detailed cross section of the invention through section 4—4 of FIG. 1 showing the needle retracting mechanism in greater detail;

FIG. 5 is a perspective view of the bead attached to the stylet of the invention;

FIG. 6 is an end view of the bead of FIG. 5;

DETAILED DESCRIPTION

Figure 7:
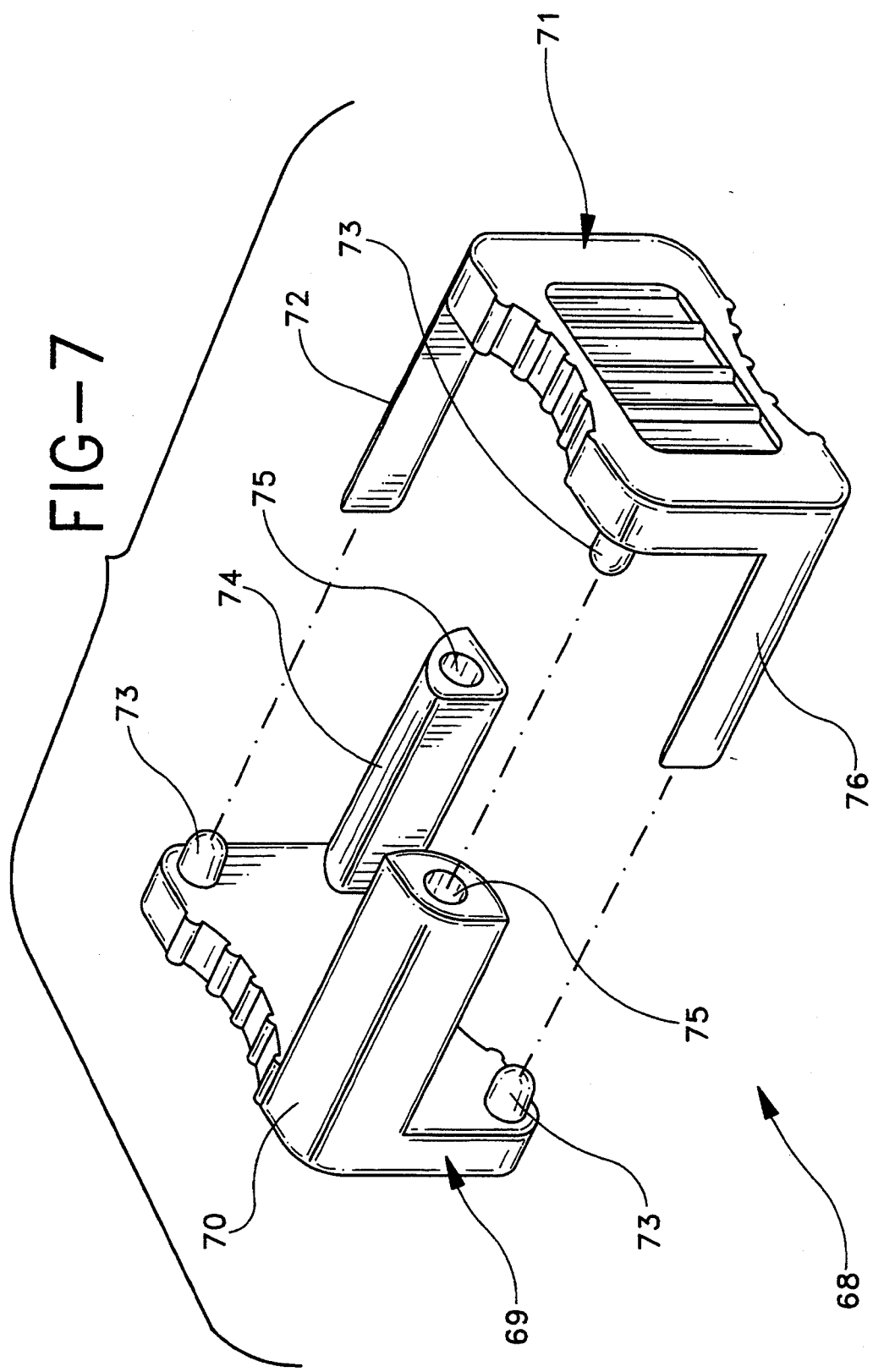
FIG. 7 is an exploded view of the needle advancer of the invention.

The following is a description of a preferred embodiment of the invention. It is intended to be illustrative and not limiting. The full scope of the invention is to be determined by reference to the claims and their equivalents.

Catheter introducer 10 is a type described in U.S. Pat. No. 5,163,913 and has the following basic components: catheter 12, winged intermediate member 14 and tube 16. Catheter 12 has a proximal end 18, a distal tip 20 and a lumen 22 extending from the proximal end to the distal end. Intermediate member 14 has a tubular part 48 having proximal end 44 and distal end 46. Proximal end 18 of catheter 12 is secured to distal end 46 of intermediate member 14. Tubular part 48 has an axial lumen 50 extending between proximal end 44 and distal end 46 such that lumen 22 of catheter 12 is in fluid communication with lumen 50 (see FIG. 2). Intermediate member 14 is provided with wings 40 and 42.

Secured to proximal end 44 of intermediate part 14 is transparent tube 16 having proximal end 52 and distal end 54. Lumen 56 extends between proximal end 52 and distal end 54. Lumen 56 is in fluid communication with lumen 22 of catheter 12 via lumen 50 of intermediate member 14 (see FIG. 2). Tube 16 is flexible, preferably being made of PVC. Tube 16 is made up of three members namely first (distal) tube 17, tubular section (intermediate) 62 and second (proximal) tube 19. First and second tubes 17 and 19 are attached to tubular member 62 as shown in FIGS. 2 and 3. In a less preferred embodiment, Tube 16 is unitary and tubular member 62 is glued over it. Tubular section 62 has proximal end 64 and distal end 66. Tubular section 62 is made up of a rigid hard plastic or metal material which is not easily bent.

Initially disposed axially within the lumen of catheter 12 is needle 24 having a proximal end 26, a sharp distal tip 28 and an axial lumen 30 extending between proximal end 26 and distal tip 28. Secured to proximal end 26 is a stylet 32 having proximal end 34 and distal end 36. Secured to proximal end 34 is an object in the form of a bead 38. In the initial position just described, proximal end 26 of needle 24 lies within lumen 50 of intermediate member 14. Distal tip 28 protrudes from distal tip 20 of catheter 12. Stylet 32 lies generally within lumen 56. Bead 38 is slidable axially along lumen 56. Since bead 38 partially occludes lumen 56, it is provided with grooves 39, 41, 43 and 45 which facilitate fluid flow through bead 38 (See FIGS. 5 and 6). Tube 16 can be squeezed adjacent bead 38. Squeezing tube 16 causes bead 38 to move axially along lumen 56 of the tube, thereby retracting needle 24. The length of first and second tubes 17 and 19 are such that when needle 24 is retracted, needle tip 28 lies within tubular section 62 as shown in FIG. 3.

Secured to proximal end 52 of tube 16 is luer connector 58 which allows catheter introducer 10 to be connected with medical tubing in a well known manner.

Mounted on the outside of tube 16 is retractor 68 which interacts with bead 38, restricting the scope of its movement within lumen 56 such that bead 38 moves along lumen 56 when retractor slides along tube 16. Retractor 68 is provided with four ribs 70, 72, 74 and 76 which confine bead 38 by squeezing tube 16 in the vicinity of bead 38 as shown in FIG. 4. Ribs 70, 72, 74 and 76 are designed such that bead 38 can be moved axially along tube 16 in one direction only. Ribs 70, 72, 74 and 76 are respectively provided with arcuate surfaces 80, 82, 84, 86 facing proximal end 52. On the opposite sides of ribs 70, 72, 74 and 76 are angular surfaces 90, 92, 94 and 96 facing distal end 54. Retractor 68 is made of two molded members 69 and 71 shown in the exploded view of FIG. 7. Members 69 and 71 are placed in alignment by the interaction of male parts 73 and female parts 75 as shown in FIG. 7.

When retractor 38 is urged in the direction of distal end 54, angular surfaces 90, 92, 94 and 96 dig into the flexible wall 60 of tube 16, thus preventing retractor 68 and hence bead 38 from moving in the distal direction. Since retractor 68 can move only in the proximal direction, bead 38, stylet 32 and needle 24 can only be moved in the proximal direction along the axis of catheter introducer 10. Once retracted, needle 24 cannot be advanced. Luer connector 52 prevents further movement of retractor 68 in the proximal direction.

Catheter introducer 10 is used as follows: With needle 24 in the initial position, protruding from distal tip 20 of catheter 12, the user grasps wings 40 and 42 between the thumb and the index finger, bringing the wings together and thus gripping needle 24 in a manner well known in the art. The sharp distal tip of needle 24 is used to pierce the patient's skin and thereafter a blood vessel. If a blood vessel is pierced, the user will observe a "flash back" of blood near proximal end 54 of tube 16. Once flashback has been observed, the user advances catheter 12 slightly in order to hood needle tip 28. Needle 24 and catheter 12 are then further advanced into the blood vessel. Once catheter 12 has been correctly placed in the blood vessel, needle 24 is retracted by sliding retractor 68 in the proximal direction. Needle 24 is retracted until sharp distal tip 28 is aligned with tubular section 62. Due to the features of retractor 68 as described above, needle 24 cannot be advanced back along tube 16. Tip 28 of needle 24 is thus trapped within tubular section 62. Needle 24 thus no longer poses a threat of causing an accidental needle stick.

The assembly of needle 24, stylet 32 and bead 38 remains in tube 16 while catheter 12 remains in the patient's blood vessel. When catheter 12 is removed, since needle 24 is securely confined in tubular section 62, catheter assembly 12 can be disposed of with relatively little risk of contamination, subsequent needle stick injury and resultant infection.

I claim:

1. A catheter introducer assembly comprising:
   a catheter having a proximal end, a distal end and a lumen extending there between;
   a flexible tube having a proximal end, a distal end and a lumen extending there between, the lumen of the tube being in fluid communication with the lumen of the catheter;
   an introducer needle having a proximal end and a distal end the needle being axially disposable in the catheter lumen;
   an object connected to the proximal end of the needle, the object partially occluding the lumen of the tube and being slidable in the tube such that squeezing the tube adjacent the object causes the object to move axially in the lumen of the tube.

2. The catheter introducer assembly of claim 1 further comprising a stylet connecting the proximal end of the needle to the object.

3. The catheter introducer assembly of claim I further comprising a retractor slidably mounted on the tube and mechanically linked to the object, such that the retractor squeezes the tube adjacent the object and such that sliding the retractor axially along the tube causes the object to slide axially in the lumen of the tube.

4. The catheter introducer assembly of claim 3 further comprising means for preventing the retractor from sliding in a distal direction.

5. The catheter assembly of claim 1 further comprising a shield for shielding the distal end of the needle, the shield being mounted on the tube proximal of the distal end of the tube.

6. The catheter assembly of claim 1 wherein the object is a bead.

7. The catheter assembly of claim 3 wherein the retractor comprises means for confining the object such that the object moves axially along the lumen of the tube when the retractor moves axially along the tube.

8. The catheter assembly of claim 7 wherein the means for confining comprise a plurality of ribs for squeezing the tube.

9. The catheter assembly of claim 3 wherein the retractor is adapted to permit the object to slide in a proximal direction but not in a distal direction.

10. The catheter assembly of claim 8 wherein the ribs have arcuate surfaces facing in a proximal direction.

11. The catheter assembly of claim 8 wherein the ribs have angular surfaces facing in a distal direction.

12. The catheter assembly of claim 1 wherein the object is provided with at least one groove to facilitate fluid flow through the tube.

13. The catheter assembly of claim 6 wherein the bead is provided with at least one groove to facilitate fluid flow through the tube.

14. A method of retracting a catheter introducer needle, the method comprising the steps of:
   connecting the catheter introducer needle to an object;
   enclosing the object within a flexible tube such that the object is axially slidable in the tube;
   squeezing the tube adjacent the object;
   imparting a substantially axial force to the tube adjacent the object such that the force is transmitted to the object, thereby moving the object axially along the tube and retracting the introducer needle.

15. The method of claim 14 further comprising the step of bringing the tip of the needle into alignment with a rigid shield on retraction of the needle.

* * * * *